US009937068B2

(12) United States Patent
Vial et al.

(10) Patent No.: US 9,937,068 B2
(45) Date of Patent: Apr. 10, 2018

(54) CRIMPING METHOD FOR BIORESORBABLE STENTS

(71) Applicant: Arterial Remodeling Technologies, S.A., Noisy le Roi (FR)

(72) Inventors: Beatrice Vial, Chargey les Gray (FR); Machiel van der Leest, Paris (FR)

(73) Assignee: ARTERIAL REMODELING TECHNOLOGIES SA (FR)

( * ) Notice: Subject to any disclaimer, the term of this patent is extended or adjusted under 35 U.S.C. 154(b) by 56 days.

(21) Appl. No.: 14/438,362

(22) PCT Filed: Oct. 24, 2013

(86) PCT No.: PCT/EP2013/072247
§ 371 (c)(1),
(2) Date: Apr. 24, 2015

(87) PCT Pub. No.: WO2014/064183
PCT Pub. Date: May 1, 2014

(65) Prior Publication Data
US 2015/0257907 A1    Sep. 17, 2015

Related U.S. Application Data

(60) Provisional application No. 61/718,549, filed on Oct. 25, 2012.

(51) Int. Cl.
*A61F 2/89* (2013.01)
*A61F 2/958* (2013.01)
*A61F 2/915* (2013.01)
*A61F 2/95* (2013.01)

(52) U.S. Cl.
CPC .............. *A61F 2/89* (2013.01); *A61F 2/95* (2013.01); *A61F 2/958* (2013.01); *A61F 2/915* (2013.01); *A61F 2002/9155* (2013.01); *A61F 2002/91558* (2013.01); *A61F 2002/9522* (2013.01); *A61F 2002/9583* (2013.01); *A61F 2210/0004* (2013.01); *Y10T 29/49925* (2015.01)

(58) Field of Classification Search
CPC .................................. A61F 2/95; A61F 2/958
USPC .............................................. 623/1.11–1.48
See application file for complete search history.

(56) References Cited

U.S. PATENT DOCUMENTS

| 5,836,965 | A | 11/1998 | Jendersee et al. |
| 5,976,181 | A | 11/1999 | Whelan et al. |
| 6,402,777 | B1 * | 6/2002 | Globerman ............... A61F 2/91 623/1.11 |
| 6,942,681 | B2 * | 9/2005 | Johnson ................ A61F 2/958 606/194 |

(Continued)

FOREIGN PATENT DOCUMENTS

| WO | 2004019768 | 3/2004 |
| WO | 2005096992 | 10/2005 |

OTHER PUBLICATIONS

ISA to corresponding International Appl. No. PCT/EP2013/072247; 3 pages.

*Primary Examiner* — Suzette J Gherbi
(74) *Attorney, Agent, or Firm* — Tarolli, Sundheim, Covell & Tummino LLP

(57) ABSTRACT

The present patent application relates to a method of crimping a tubular stent having a stent lumen onto an inflatable balloon of a stent delivery catheter.

7 Claims, 5 Drawing Sheets

(56) References Cited

U.S. PATENT DOCUMENTS

| | | | |
|---|---|---|---|
| 7,731,740 B2* | 6/2010 | LaFont | A61F 2/82 264/319 |
| 7,743,481 B2 | 6/2010 | LaFont et al. | |
| 8,062,465 B1* | 11/2011 | Huang | A61F 2/958 156/294 |
| 8,123,793 B2 | 2/2012 | Roach et al. | |
| 8,141,226 B2 | 3/2012 | Seyler et al. | |
| 8,752,261 B2* | 6/2014 | Van Sciver | A61F 2/958 29/272 |
| 9,199,408 B2* | 12/2015 | Wang | B29C 53/02 |
| 2002/0138966 A1 | 10/2002 | Motsenbocker | |
| 2007/0100431 A1* | 5/2007 | Bonsignore | A61F 2/915 623/1.15 |
| 2007/0239251 A1* | 10/2007 | Prabhu | A61F 2/915 623/1.2 |
| 2009/0054837 A1* | 2/2009 | Von Holst | A61L 29/16 604/103.08 |
| 2012/0010693 A1* | 1/2012 | Van Sciver | A61F 2/958 623/1.11 |
| 2012/0035709 A1* | 2/2012 | Young | A61F 2/91 623/1.16 |
| 2012/0079706 A1* | 4/2012 | Knott | A61F 2/958 29/516 |
| 2012/0102708 A1* | 5/2012 | Strauss | A61F 2/91 29/428 |
| 2012/0261858 A1* | 10/2012 | Roberts | A61F 2/915 264/249 |
| 2013/0000548 A1* | 1/2013 | Eidenschink | A61F 2/95 118/44 |
| 2013/0066268 A1* | 3/2013 | Von Holst | A61L 29/16 604/103.08 |
| 2013/0310913 A1* | 11/2013 | Wang | A61F 2/958 623/1.11 |
| 2013/0333193 A1* | 12/2013 | Pacetti | A61F 2/958 29/447 |
| 2014/0013575 A1* | 1/2014 | Wang | A61F 2/95 29/505 |
| 2015/0074975 A1* | 3/2015 | Huang | A61F 2/958 29/446 |
| 2015/0282969 A1* | 10/2015 | Pacetti | A61F 2/958 29/515 |
| 2015/0320577 A1* | 11/2015 | Zheng | A61F 2/82 623/1.15 |
| 2016/0030216 A1* | 2/2016 | Wang | A61L 31/06 29/516 |
| 2016/0038320 A1* | 2/2016 | Wang | B29C 53/02 29/516 |
| 2016/0067460 A1* | 3/2016 | Hanisch | A61M 25/1006 604/103.11 |
| 2016/0228267 A1* | 8/2016 | Pacetti | A61F 2/82 |
| 2016/0317790 A1* | 11/2016 | Ruebben | A61M 25/0054 |
| 2016/0374840 A9* | 12/2016 | Trollsas | A61F 2/91 29/516 |

* cited by examiner

CRIMPING METHOD FOR BIORESORBABLE STENTS

FIELD OF THE INVENTION

The present invention relates to a method for crimping a vascular stent onto a stent delivery catheter. The crimping method disclosed is particularly advantageous for crimping a bioabsorbable or bioresorbable polymeric vascular stent onto an inflatable balloon of a stent delivery catheter.

BACKGROUND OF THE INVENTION

In recent decades, vascular stenting has become an important therapy for treating occlusive vascular disease, including coronary artery disease, carotid artery disease and peripheral artery disease. A stent, also known as a vascular scaffold, is a tubular structure that is used, sometimes in conjunction with an angioplasty balloon catheter, to open up a stenosis or narrowing in a blood vessel and to hold the blood vessel open to allow improved blood flow. Stents are also used to treat strictures or narrowings in body passages other than blood vessels. Vascular stents are typically grouped into two general categories: balloon expendable stents and self-expanding stents. The bioresorbable vascular stent used in the present invention can be considered to be a hybrid of these two types. The bioresorbable vascular stent is heat treated to have a shape memory that makes the stent expand toward its deployed diameter. This behavior is temperature dependent. Above the glass transition temperature Tg of the stent material, the stent expands quickly, but at body temperature, the stent expands more slowly. An inflatable balloon is therefore used to accelerate the deployment of the stent, but even after deployment, the stent will continue to expand slightly, which assists in apposing the stent struts to the vessel wall. The stent could therefore be considered to be a balloon-assisted self-expanding stent or a self-apposing balloon expandable stent. For the crimping process however, the bioresorbable vascular stent can be treated much like a balloon expandable stent.

Typically, a balloon expandale stent is mounted on a stent delivery catheter by crimping (i.e. squeezing) the stent onto an inflatable balloon located near the distal end of the catheter.

Specialized crimping devices and automated machines have been devised for crimping stents onto balloon catheters. See, for example: U.S. Pat. No. 8,141,226; PCT International Application WO 2004/019768 and U.S. Patent Application 2002/0138966. Where allowed, these and all patents and patent applications referred to herein are hereby incorporated by reference. The stent crimping devices described in these patents can be modified for use with the crimping method of the present invention by adding controlled heating and cooling the crimp head.

Most balloon expandable stents used today are metal stents. However, there is an emerging field of bioabsobable or bioresorbable polymeric vascular stents. The terms bioabsorbable and bioresorbable are used interchangeably in the medical device industry to describe a material that, after implantation in the body, breaks down over time and is absorbed or resorbed by the surrounding tissues. Typical materials for bioabsorbable or bioresorbable stents include polylactic acid (PLA) and polyglycolic acid (PGA) polyglactin (PLAGA copolymer). Additional stent materials suitable for the present invention are described in U.S. Pat. No. 7,731,740 and PCT International Application WO 2005/096992. In general, a polymer with a glass transition temperature (Tg) of a least 45° C. is preferred.

Polymeric vascular stents present particular challenges in stent crimping. U.S. Pat. No. 7,743,481 describes an apparatus and method that are particularly adapted for crimping polymeric vascular stents. This stent crimping apparatus can be modified for use with the crimping method of the present invention by adding controlled heating and cooling.

Various methods have been devised for crimping balloon expandable stents that involve a step of inflating the balloon on the catheter during the crimping process. Examples of these methods are described in the following and patent applications: U.S. Pat. No. 5,836,965 (cf. FIG. 3); U.S. Pat. No. 5,976,181; and U.S. Pat. No. 8,123,793 (cf. FIG. 4).

Generally, the methods described in these patent references are not suitable for application to bioabsorbable or bioresorbable polymeric vascular stents. One fundamental difference between metallic stents and polymeric stents is that tubular metallic stents are typically fabricated at a diameter that is just slightly larger than their undeployed or crimped diameter. During the crimping step, the diameter of the stent only needs to be reduced by a small amount. Thus, when the balloon is inflated during the crimping process, it cannot assume its fully expanded diameter because it is constrained by the stent and the crimping apparatus. If the balloon were to be fully inflated it would impart irreversible plastic deformation to the stent struts, which would be highly deleterious to the stent. On the other hand, tubular polymeric stents are fabricated at a diameter that is close to their deployed of fully expanded diameter. During the crimping process, the diameter of the stent must be reduced from the deployed or fully expanded diameter to the undeployed or crimped diameter. Elevating the temperature of the polymeric stent at or above Tg during crimping avoids the problem of irreversible plastic deformation that occurs with metallic stents. Because it takes into account these differences, the crimping method of the present invention is particularly advantageous for crimping a bioabsorbable or bioresorbable polymeric vascular stent onto an inflatable balloon of the stent delivery catheter.

BRIEF DESCRIPTION OF THE INVENTION

Figure 1:
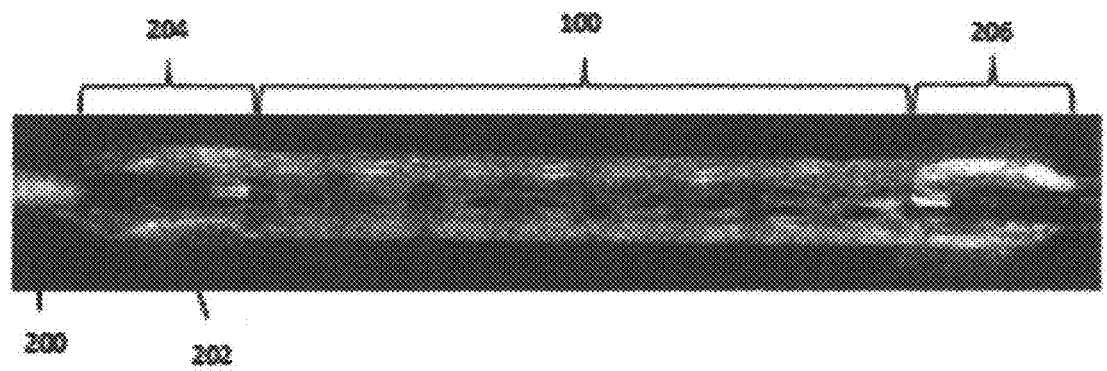
FIG. 1 is a photograph of a bioresorbable polymeric vascular stent crimped onto the balloon of a stent delivery catheter according to the method of the present invention.

Inventors herein provide a method of crimping a tubular stent having a stent lumen onto an inflatable balloon of a stent delivery catheter, the stent having a deployed diameter and a crimped diameter that is smaller than the deployed diameter. This method comprises:

inserting the inflatable balloon of the stent delivery catheter into the stent lumen of the tubular stent with the inflatable balloon at a deflated diameter and with the tubular stent at approximately the deployed diameter;

inflating the inflatable balloon of the stent delivery catheter to an inflated diameter within the stent lumen of the tubular stent;

crimping the tubular stent to the crimped diameter while maintaining inflation pressure within the inflatable balloon of the stent delivery catheter; and deflating the inflatable balloon of the stent delivery catheter while maintaining the tubular stent at the crimped diameter.

The herein described method can further comprise a step of heating the tubular stent to a temperature at or above the glass transition temperature prior to the crimping step and/or a step of cooling the tubular stent to a temperature below the glass transition temperature after the crimping step.

In a particular embodiment of the present invention, the inflatable balloon of the stent delivery catheter is inflated within the stent lumen of the tubular stent with an inflation pressure typically between 0.1 to 5 bars or 0.1 to 2.5 bars, preferably of approximately 0.2 to 2.0 bars, prior to the crimping step of the method according to the present invention and maintained at this inflation pressure during the crimping step. Preferably, the method further comprises after the crimping step and prior to the deflating step, a step of increasing the inflation pressure of the inflatable balloon of the stent delivery catheter within the stent lumen of the tubular stent to an inflation pressure of approximately 3.0 to 7.0 bars while maintaining the tubular stent at the crimped diameter.

In another particular embodiment of the present invention, the method of the invention further comprises prior to inserting the inflatable balloon of the stent delivery catheter into the stent lumen of the tubular stent, a step of inserting the tubular stent into a crimping machine at approximately the deployed diameter and a step of precrimping the tubular stent to a precrimped diameter that is slightly smaller than the deployed diameter. This method can further comprise after the deflating step, a step of removing the tubular stent and the inflatable balloon of the stent delivery catheter from the crimping machine.

A preferred method of the invention comprises:

prior to inserting the inflatable balloon of the stent delivery catheter into the stent lumen of the tubular stent, inserting a tubular stent formed from a polymer having a glass transition temperature into a crimping machine at approximately the deployed diameter and precrimping the tubular stent to a precrimped diameter that is slightly smaller than the deployed diameter;

prior to the crimping step, heating the tubular stent to a temperature at or above the glass transition temperature;

prior to the crimping step, inflating the inflatable balloon of the stent delivery catheter within the stent lumen of the tubular stent with an inflation pressure typically between 0.1 to 2.5 bars, preferably of approximately 0.2 to 2.0 bars and maintaining this inflation pressure during the crimping step;

after the crimping step and prior to the deflating step, increasing the inflation pressure of the inflatable balloon of the stent delivery catheter within the stent lumen of the tubular stent to an inflation pressure of approximately 3.0 to 7.0 bars while maintaining the tubular stent at the crimped diameter and cooling the tubular stent to a temperature below the glass transition temperature; and after the deflating step, removing the tubular stent and the inflatable balloon of the stent delivery catheter from the crimping machine.

Another object of the invention is an apparatus comprising:

a tubular stent having a multiplicity of stent struts arranged around a stent lumen of the tubular stent and a multiplicity of interstices between the stent struts, the tubular stent being positioned at an undeployed, crimped diameter; and an inflatable balloon positioned within the stent lumen of the tubular stent, the inflatable balloon being positioned at an undeployed, deflated diameter with a wall material of the inflatable balloon arranged into a multiplicity of folds;

wherein the multiplicity of stent struts are evenly distributed around a circumference of the tubular stent and the wall material of the inflatable balloon is evenly distributed around the circumference of the tubular stent.

In the previously described apparatus, the wall material of the inflatable balloon can protrude into the multiplicity of interstices between the stent struts.

In a particular embodiment of the invention, an approximately equal amount of the wall material of the inflatable balloon protrudes into each the multiplicity of interstices between the stent struts.

In another particular embodiment of the invention, the stent can have a proximal end and a distal end and the wall material of the inflatable balloon can be configured to form a proximal bumper of increased diameter positioned beyond the proximal end of the stent and a distal bumper of increased diameter positioned beyond the distal end of the stent.

The multiplicity of stent struts can be each in contact with the wall material of the inflatable balloon. The multiplicity of stent struts can also be configured i) to enclose a multiplicity of closed cells arranged around a circumference of the tubular stent or ii) to enclose a multiplicity of closed cells arranged in rings around a circumference of the tubular stent, a plurality of linking struts connecting adjacent rings of closed cells.

The tubular stent used in the context of the invention typically comprises a bioresorbable material, preferably a bioresorbable polymer. The tubular stent is advantageously formed from a material having a glass transition temperature (Tg), advantageously a glass transition temperature (Tg) of at least 45° C. Preferably the tubular stent comprises a poly (lactic acid) polymer. Preferably the tubular stent comprises an antiproliferative agent.

DETAILED DESCRIPTION OF THE INVENTION

A prior art method used by applicant for crimping a PLA bioresorbable stent on a semicompliant angioplasty balloon includes the following steps:

1. Loading the PLA stent in a preheated stainless steel crimp head (at or above the polymer glass transition temperature Tg) at a pre-crimp diameter of approximately 0.2 mm less than the PLA stent cut component diameter;
2. After a preheating period, the PLA stent diameter is reduced to and maintained at crimp diameter;
3. Immediately after reaching crimp diameter, the PLA stent is cooled down to below Tg (typically to room temperature) while increasing the balloon pressure, preferably between approximately 3.0 to 7.0 bars, to created bumpers at the balloon cone level.

By contrast, the improved crimping method of the present invention includes the following steps:
1. Loading the PLA stent in a preheated stainless steel crimp head (at or above the polymer glass transition temperature Tg);
2. Precrimping the stent to a diameter of approximately 0.2 mm less than the PLA stent cut component diameter (which is just enough to grip the stent within the crimp head);
3. After a time delay of approximately 30-180 seconds to allow the stent material to heat up in the crimp head, inserting the balloon of a stent delivery catheter into the lumen of the stent and fully inflating the balloon at a low pressure typically between approximately 0.2 to 5.0 bars (for example 1, 2, 3 or 4 bars), preferably between approximately 0.2 to 2.0 bars;
4. After a sufficient preheating period to heat the stent material to at or above the polymer glass transition temperature Tg, reducing the diameter of the PLA stent together with the inflated balloon using the crimp head and maintaining the stent at the crimped diameter;
5. Immediately after reaching the crimped diameter, cooling the PLA stent down to below Tg (typically to room temperature) while increasing the balloon pressure, preferably between approximately 3.0 to 7.0 bars, to created bumpers at the balloon cone level; and
6. Releasing the pressure in the balloon and removing the stent delivery catheter with the stent crimped on the balloon from the crimp head.

The improved crimping method provides a number of advantages over the prior art:
1. Significantly increased stent retention;
2. Increased homogeneity of the crimped stent since the inflated balloon guides the PLA stent in a rubbery state (at around Tg), resulting in fewer defects due to crimping;
3. Improved stent expansion since the balloon is pre-fit (in phase) to the final stent diameter leading to an increased homogeneity of the expanded stent;
4. Improved guidance of the crimped stent while tracking as the balloon penetrates in between stent struts;
5. Significantly increased tracking time in the artery vasculature over 30 minutes, which is important because, as noted above, PLA stents begin to slowly expand when heated up to body temperature (37° C.).

Figure 8:
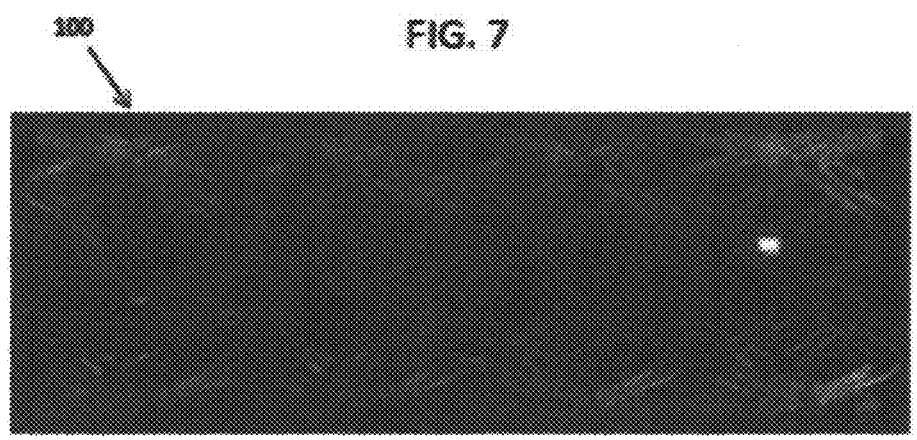
FIG. 8 is a photograph of a deployed bioresorbable polymeric vascular stent.
Figure 10:
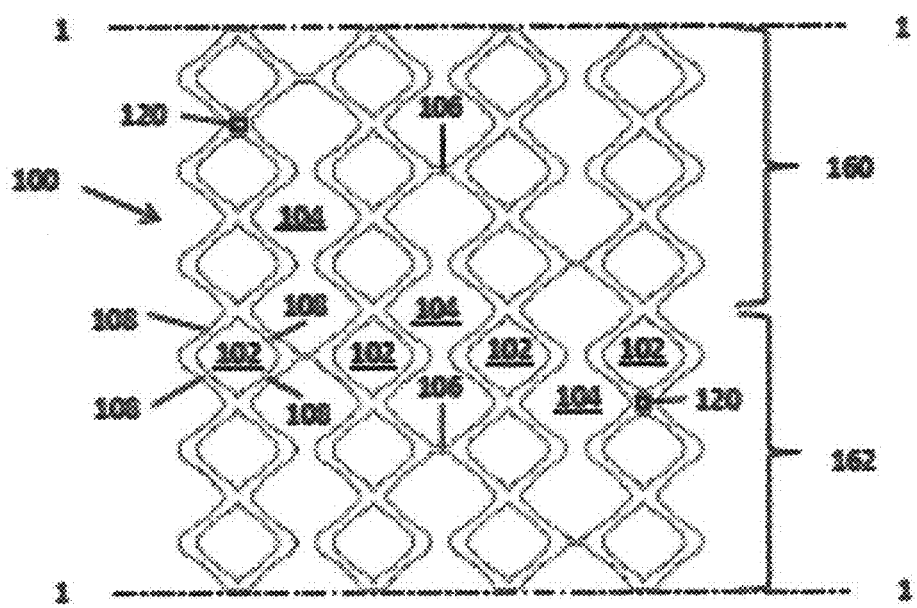
FIG. 10 illustrates a deployed vascular stent that was previously crimped according to the stent crimping method of the present invention. The stent is laid out flat to show the even deployment of the stent.

FIGS. 8 and 10 illustrate a vascular stent 100 suitable for use with the crimping method of the present invention. The stent 100 is generally manufactured in a tubular configuration, as shown in FIG. 8, but FIG. 10 has been drawn as if the stent 100 has been cut longitudinally along line 1-1 and laid out flat to more clearly illustrate the structure of the stent 100.

Preferably, the stent 100 is made from a bioabsorbable or bioresorbable polymer having a Tg of at least 45° C. The stent 100 can be manufactured in a many different possible designs. This illustrative embodiment shows a stent 100 with a combination of closed cells 102 for structural strength in the circumferential direction (i.e. radial strength) and open cells 104 for flexibility in the longitudinal direction. Each of the closed cells 102 is bordered by four approximately-linear struts 108 whose ends are joined together to form a diamond, rhombus or lozenge-shaped cell 102. The illustrated stent 100 has six cells 102 in the circumferential direction and four cells 102 in the longitudinal direction. This stent configuration can be envisioned as having four circumferential rings with six closed cells 102 each, which are joined by two linking struts 106 between each pair of adjacent rings. Many other stent, cell and strut configurations are possible. Optionally, the stent 100 may include one or more radiopaque markers 120. Furthermore, the bioresorbable stent may optionally include an antiproliferative agent, such as paclitaxel, sirolimus (rapamycin) or another limus-family drug, in the form of a coating or compounded into the polymer for extended release.

FIG. 1 is a photograph of a bioresorbable polymeric vascular stent 100 crimped onto the balloon 202 of a stent delivery catheter 200 utilizing the method of the present invention.

Figure 2:
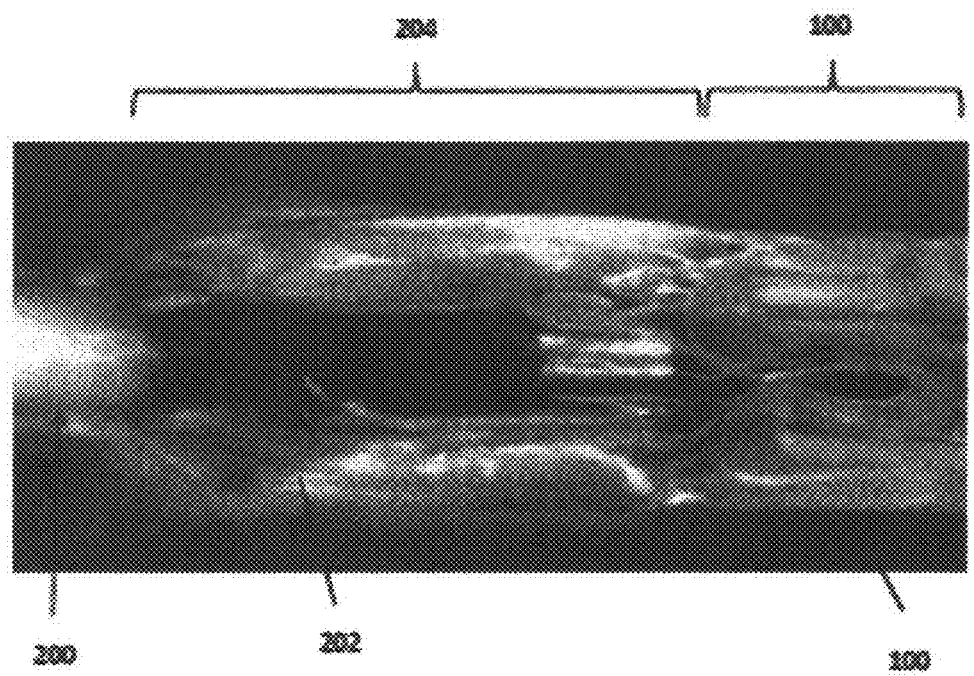
FIG. 2 is an enlarged detail photograph of a proximal portion of the inflatable balloon and the vascular stent of FIG. 1, showing a bumper at the balloon cone level that is formed during the crimping process.

FIG. 2 is an enlarged detail photograph of a proximal portion of the inflatable balloon 202 and the vascular stent 100 of FIG. 1, showing a proximal bumper 204 and a distal bumper 206 that are formed at the proximal and distal cone portions of the inflatable balloon 202 during the second inflation step of the crimping process. The proximal bumper 204 and distal bumper 206 help to retain the stent 100 on the stent delivery catheter 200 during insertion and advancement of the catheter 200.

Figure 3:
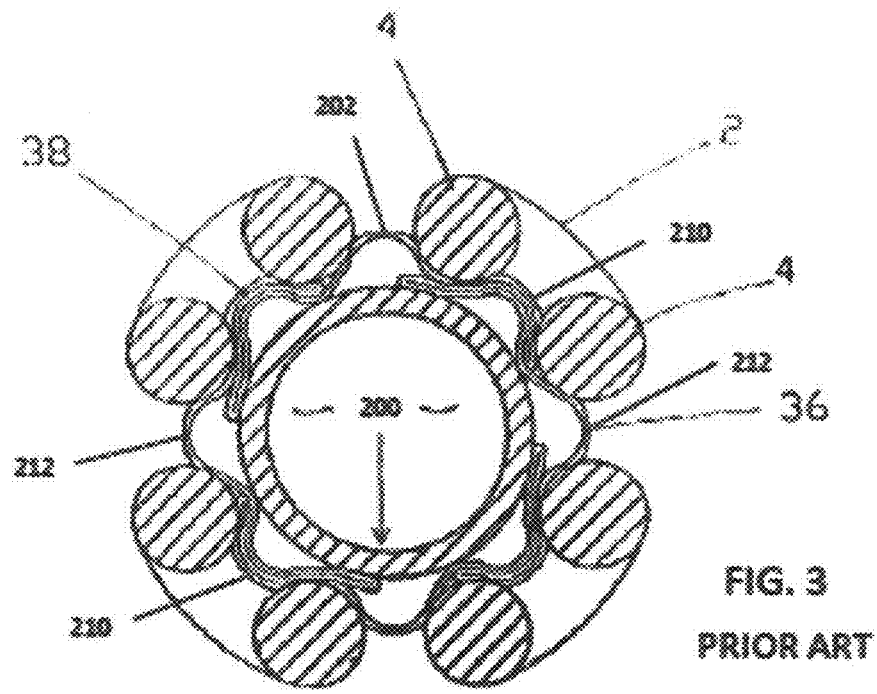
FIG. 3 is a cross section of a stent crimped onto the balloon of a stent delivery catheter using a prior art crimping method according to U.S. Pat. No. 5,836,965.

FIG. 3 is a cross section of a metallic stent 4 that was crimped onto the balloon 202 of a stent delivery catheter 200 using a prior art crimping method according to U.S. Pat. No. 5,836,965. It is evident that the balloon 202 was folded into wings prior to partially inflating the balloon 202 inside the stent 4 during crimping. Note that the balloon material 202 is not evenly distributed in between the stent struts 108. In some of the interstices between stent struts 108 there is a great deal of redundancy of balloon material 210, whereas in other interstices between stent struts 108 there is essentially no redundancy of balloon material 212. The uneven distribution of the balloon material 202 in between the stent struts 108 can lead to uneven deployment of the stent 4 when the balloon 202 is inflated.

Figure 4:
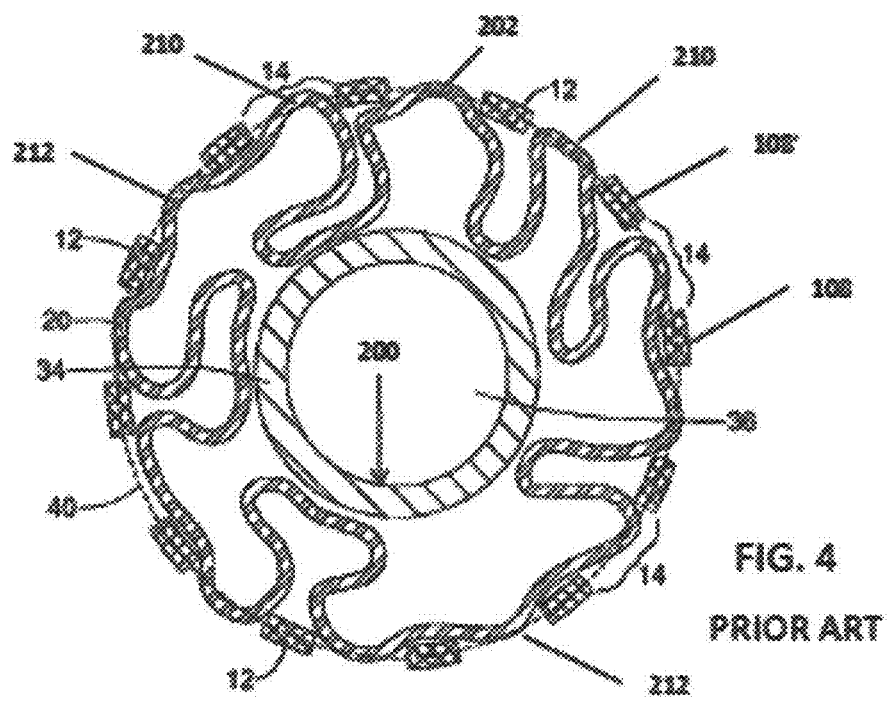
FIG. 4 is a cross section of a stent crimped onto the balloon of a stent delivery catheter using another prior art crimping method according to U.S. Pat. No. 8,123,793.

FIG. 4 is a cross section of a metallic stent 12 that was crimped onto the balloon 202 of a stent delivery catheter 200 using another prior art crimping method according to U.S. Pat. No. 8,123,793. In this example, the balloon 202 is irregularly folded underneath the stent 12. As in the above example, the balloon material 202 is not evenly distributed in between the stent struts 108. In some of the interstices between stent struts 108 there is a great deal of redundancy of balloon material 210, whereas in other interstices between stent struts 108 there is essentially no redundancy of balloon material 212. Also note that some of the stent struts 108 are in contact with the balloon material, while others 108' are not. The uneven distribution of the balloon material 202 in between the stent struts 108 can lead to uneven deployment of the stent 100 when the balloon 202 is inflated.

Figure 9:
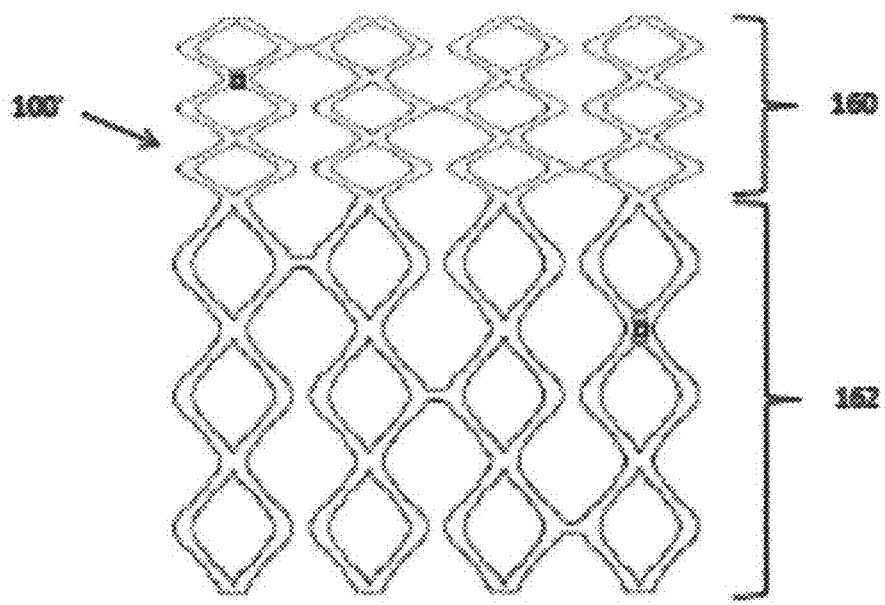
FIG. 9 illustrates a deployed vascular stent that was previously crimped according to prior art methods. The stent is laid out flat to show the uneven deployment of the stent.

FIG. 9 illustrates a deployed vascular stent 100' that was previously crimped according to prior art methods, such as the examples described above. The stent 100' is laid out flat to show the uneven deployment of the stent 100'. The upper portion 160 represents an area of the stent 100' where there was not enough redundancy of balloon material between stent struts, which causes this area of the stent to be underdeployed. The lower portion 162 represents an area of the stent where there was too much redundancy of balloon material between stent struts, which causes this area of the stent to be overdeployed or overstretched. Uneven deployment of the stent can compromise the structural strength of the stent 100'. For drug eluting stents, uneven deployment of the stent can cause additional problems. Some areas of the vascular wall where the stent is underdeployed can receive too much antiproliferative drug per surface area, whereas other areas of the vascular wall where the stent is overdeployed may not receive enough of the antiproliferative drug per surface area.

Figure 5:
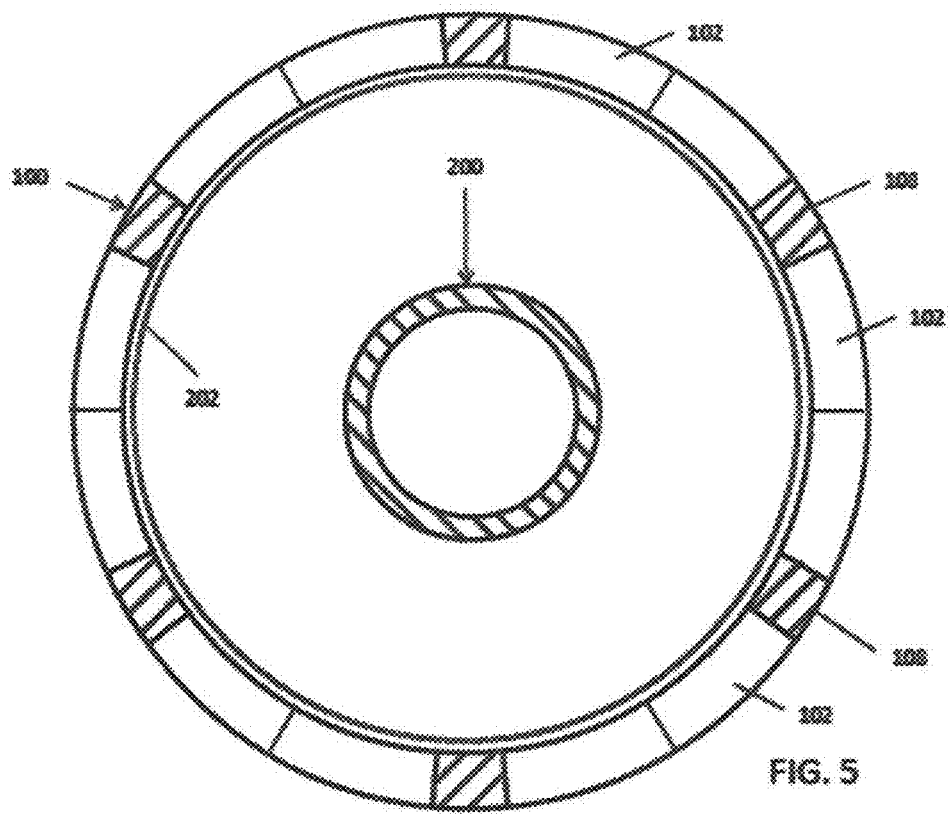
FIG. 5 is a cross section sowing the balloon inflation step of the stent crimping method of the present invention.

FIG. 5 is a cross section showing the balloon inflation step of the stent crimping method of the present invention. Note that the stent 100 is at or very close to the fully deployed diameter of the stent 100 and the inflated balloon 202 is also at or very close to its nominal inflated diameter. The balloon material 202 is in-phase with the stent struts 108, that is, the balloon material 202 is evenly distributed in between the stent struts 108. Another way to describe this is that there is a 1-to-1 mapping between the balloon material and the circumference of the stent.

Figure 6:
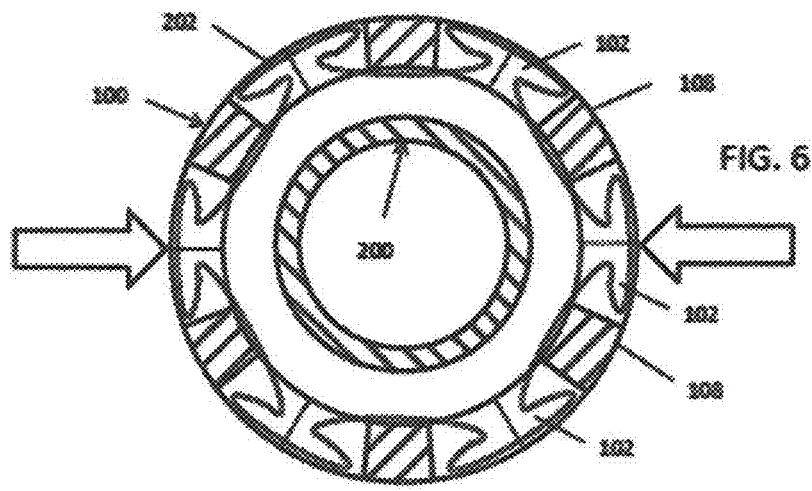
FIG. 6 is a cross section showing the crimping step of the stent crimping method of the present invention.

FIG. 6 is a cross section showing the crimping step of the stent crimping method of the present invention. During the crimping step, the inflated balloon 202 guides the stent struts 108 from the as-cut stent diameter to the crimped stent diameter and assures an evenly spaced crimped configuration. Note that, during the crimping step, the balloon material 202 remains in-phase with the stent struts 108 and that, although there is redundancy of balloon material 202, the balloon material 202 is evenly distributed in between the stent struts 108. The 1-to-1 mapping between the balloon material and the circumference of the stent is maintained as the diameter of the stent is reduced by crimping. The inflation pressure inside the balloon causes the balloon material 202 to protrude between the stent struts 108 as the diameter of the stent 100 is reduced.

Figure 7:
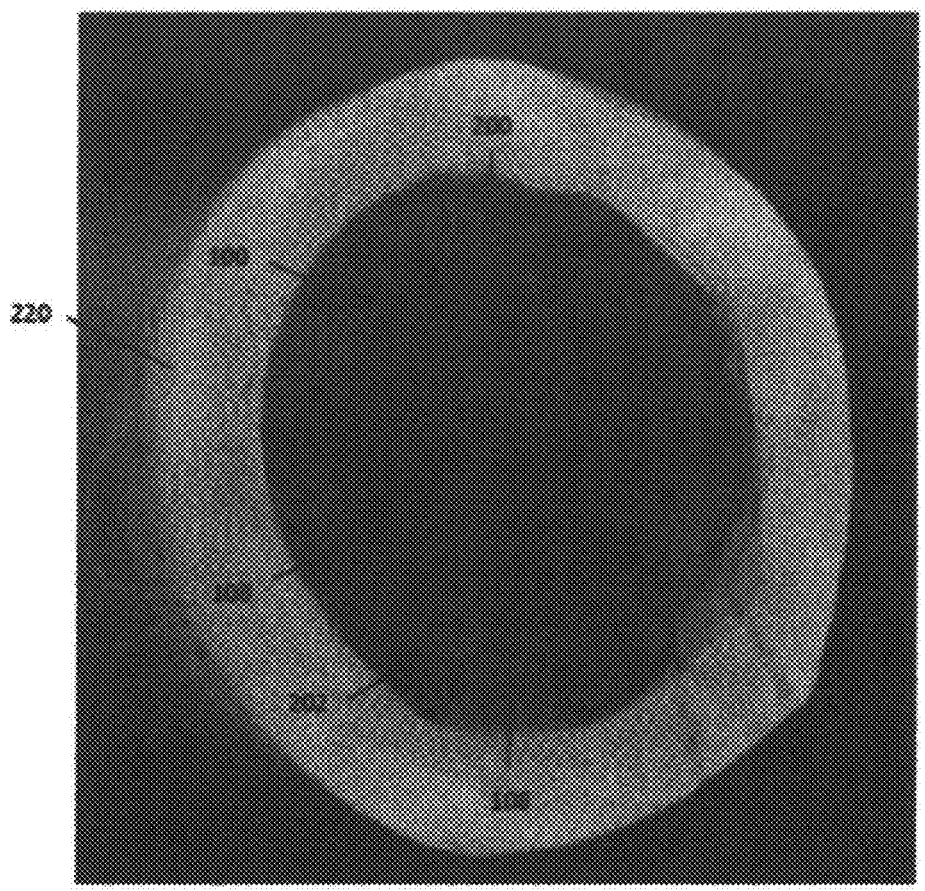
FIG. 7 is a cross section photograph showing the final result of the stent crimping method of the present invention.

FIG. 7 is a cross section photograph showing the final result of the stent crimping method of the present invention. Each of the stent struts 108 is in contact with the balloon material 202 and the balloon material 202 is evenly distributed in between the stent struts 108. The protrusion or interdigitation of the balloon material 202 between the struts 108 of the stent greatly increases the retention strength of the stent 100 on the stent delivery catheter 200, which is very important for successful delivery and deployment of the stent 100 in a patient's blood vessel. The balloon 202 with the stent 100 crimped onto it has been inserted into a tubular protection sleeve 220 that protects the assembly during packaging, sterilization and handling. In use, the stent delivery catheter 200 is inserted into the patient's vasculature to deliver the stent 100 to a stenosis or narrowing in an artery or other vessel. The balloon 202 is inflated to expand the stent 100 and appose it to the vessel wall. The balloon 202 is then deflated and the catheter 200 is withdrawn. The expanded stent 100 holds open the previously stenosed portion of the artery. However, the material of the stent 100 gradually decomposes over a period of months and is resorbed by the surrounding tissues, thus allowing the artery to remodel and return to its normal function. The bioresorbable stent does not leave behind a large amount of foreign material that might cause inflammation, which could lead to restenosis or late stent thrombosis.

FIG. 8 is a photograph of a deployed bioresorbable polymeric vascular stent 100 that was previously crimped according to the stent crimping method of the present invention. FIG. 10 illustrates the deployed vascular stent 100 of FIG. 8 with the stent laid out flat to show the even deployment of the stent 100. The stent struts 108 are evenly distributed around the surface area of the stent 100. In contrast to the prior art stent 100' of FIG. 9, the upper portion 160 and lower portion 162 of the stent 100 are evenly deployed. If the stent 100 is a drug eluting stent, the antiproliferative drug will be evenly distributed around the inner surface of the vascular wall as well.

The invention claimed is:

1. A method of crimping a bioresorbable polymeric tubular stent having a stent lumen onto an inflatable balloon of a stent delivery catheter, the stent having a multiplicity of stent struts evenly distributed around the stent lumen and a multiplicity of interstices between the stent struts, and the stent having a deployed diameter and a crimped diameter that is smaller than the deployed diameter, the bioresorbable polymer having a glass transition temperature (Tg), the inflatable balloon having a wall material arranged into a multiplicity of folds and evenly distributed around the stent lumen, and the method comprising in the following order:
   (a) inserting the inflatable balloon of the stent delivery catheter into the stent lumen of the tubular stent with the inflatable balloon at a deflated diameter and with the tubular stent at approximately the deployed diameter;
   (b) heating the tubular stent to a temperature at or above the glass transition temperature of the bioresorbable polymer;
   (c) inflating the inflatable balloon of the stent delivery catheter to an inflated diameter within the stent lumen of the tubular stent with an inflation pressure between 0.1 to 5 bars;
   (d) crimping the tubular stent from the deployed diameter to the crimped diameter while maintaining the inflation pressure within the inflatable balloon of the stent delivery catheter;
   (e) cooling the tubular stent to a temperature below the glass transition temperature while maintaining the inflation pressure within the inflatable balloon of the stent delivery catheter; and
   (f) deflating the inflatable balloon of the stent delivery catheter while maintaining the tubular stent at the crimped diameter.

2. The method of claim 1, wherein the tubular stent comprises a poly (lactic acid) polymer.

3. The method of claim 1, further comprising after the crimping step and prior to the deflating step, increasing the inflation pressure of the inflatable balloon of the stent delivery catheter within the stent lumen of the tubular stent to an inflation pressure of approximately 3.0 to 7.0 bars while maintaining the tubular stent at the crimped diameter.

4. The method of claim 1, further comprising prior to inserting the inflatable balloon of the stent delivery catheter into the stent lumen of the tubular stent, inserting the tubular stent into a crimping machine at approximately the deployed diameter and precrimping the tubular stent to a precrimped diameter that is slightly smaller than the deployed diameter.

5. The method of claim 4, further comprising after the deflating step, removing the tubular stent and the inflatable balloon of the stent delivery catheter from the crimping machine.

6. The method of claim 1, wherein the tubular stent is formed from a bioresorbable polymer having a glass transition temperature and wherein the method further comprises:

prior to inserting the inflatable balloon of the stent delivery catheter into the stent lumen of the tubular stent, inserting the tubular stent into a crimping machine at approximately the deployed diameter and precrimping the tubular stent to a precrimped diameter that is slightly smaller than the deployed diameter;

prior to the crimping step, heating the tubular stent to a temperature at or above the glass transition temperature;

prior to the crimping step, inflating the inflatable balloon of the stent delivery catheter within the stent lumen of the tubular stent with an inflation pressure of approximately 0.2 to 2.0 bars and maintaining this inflation pressure during the crimping step;

after the crimping step and prior to the deflating step, increasing the inflation pressure of the inflatable balloon of the stent delivery catheter within the stent lumen of the tubular stent to an inflation pressure of approximately 3.0 to 7.0 bars while maintaining the tubular stent at the crimped diameter and cooling the tubular stent to a temperature below the glass transition temperature; and after the deflating step, removing the tubular stent and the inflatable balloon of the stent delivery catheter from the crimping machine.

7. The method of claim 6, wherein the tubular stent comprises a poly (lactic acid) polymer.

\* \* \* \* \*